United States Patent
Ramprakash et al.

(10) Patent No.: US 11,813,043 B2
(45) Date of Patent: Nov. 14, 2023

(54) SYSTEM AND METHODS FOR DETECTION OF SUBJECTS VITALS AND PHYSIOLOGICAL SYMPTOMS VIA NON-CONTACT METHODS

(71) Applicant: STRUCTURED MONITORING PRODUCTS, INC., Elyria, OH (US)

(72) Inventors: Vikram Ramprakash, Orlando, FL (US); Kenneth Balogh, Elyria, OH (US); Dave Holden, Elyria, OH (US); Richard Sating, Elyria, OH (US)

(73) Assignee: Structured Monitoring Products, Inc., Elyria, OH (US)

( * ) Notice: Subject to any disclaimer, the term of this patent is extended or adjusted under 35 U.S.C. 154(b) by 0 days.

(21) Appl. No.: 18/062,015

(22) Filed: Dec. 5, 2022

(65) Prior Publication Data
US 2023/0172460 A1    Jun. 8, 2023

Related U.S. Application Data

(60) Provisional application No. 63/285,756, filed on Dec. 3, 2021.

(51) Int. Cl.
| | |
|---|---|
| *A61B 5/02* | (2006.01) |
| *A61B 5/0205* | (2006.01) |
| *A61B 5/00* | (2006.01) |
| *A61B 5/05* | (2021.01) |
| *A61B 5/08* | (2006.01) |
| *A61B 5/024* | (2006.01) |

(52) U.S. Cl.
CPC ............ *A61B 5/02055* (2013.01); *A61B 5/05* (2013.01); *A61B 5/7228* (2013.01); *A61B 5/0059* (2013.01); *A61B 5/024* (2013.01); *A61B 5/0816* (2013.01); *A61B 2562/0204* (2013.01); *A61B 2562/0219* (2013.01); *A61B 2562/0257* (2013.01)

(58) Field of Classification Search
None
See application file for complete search history.

(56) References Cited

U.S. PATENT DOCUMENTS

| | | | |
|---|---|---|---|
| 10,292,369 B1* | 5/2019 | Heath | A61B 5/0205 |
| 2009/0203972 A1* | 8/2009 | Heneghan | G16H 40/63 |
| | | | 600/301 |
| 2011/0237948 A1* | 9/2011 | Corn | A61B 8/0883 |
| | | | 600/443 |
| 2020/0237252 A1* | 7/2020 | Lane | G01S 13/88 |

* cited by examiner

*Primary Examiner* — Ankit D Tejani
(74) *Attorney, Agent, or Firm* — Maxwell L. Minch; Maxwell L Minch Esq. PA

(57) ABSTRACT

The present invention provides a non-contact vital sign monitoring which properly detect subject's vital signs by correcting the measured signals for reflectance and variations in distance between measurements. The present invention provides for adequate sensor numbers and types to properly monitor a subject's vitals and physiological signals. Certain aspects of the invention include the use of signal scoring methods. In such embodiments, acquired data and/or information is used for scoring a signal acquired from non-contact vital monitoring assisting in the accurate measurement of various vitals of a subject, including, without limit, a subjects temperature, cardiovascular and respiratory information. The present invention provides a viable solution for at-a-distance non-contact vital sign monitoring that overcomes the shortcomings of existing solutions known in the art.

20 Claims, 2 Drawing Sheets

Illustration 1

SYSTEM AND METHODS FOR DETECTION OF SUBJECTS VITALS AND PHYSIOLOGICAL SYMPTOMS VIA NON-CONTACT METHODS

CROSS-REFERENCE TO RELATED APPLICATIONS

This application claims priority to U.S. Provisional Patent Application 63/285,756, filed Dec. 3, 2021, entitled "SYSTEM AND METHODS FOR DETECTION OF SUBJECTS VITALS AND PHYSIOLOGICAL SYMPTOMS VIA NON-CONTACT METHODS", the contents of which are incorporated by reference as if fully set forth herein.

FIELD OF INVENTION

The present invention is related to vital sign monitoring systems that can assess the physiological and psychological state of a subject and, in particular, relates to non-contact vital sign monitoring systems that are placed at a distance from the subject, and their method of use.

BACKGROUND

Measurement of a subject's physiological health through vital sign monitoring is commonly used, and is useful, in medical diagnostics. Vital signs monitored typically include, without limit, body temperature, blood pressure, pulse (heart rate), and breathing rate (respiratory rate), and blood oxygenation of a subject. To date, these measurements are accomplished by direct contact with a subject through the use of sensors and hand-held devices.

However, problems arise in situations where the subject being measured is not accomplished very easily. In cases where the subject is an animal, it may not be safe to the medical provider to come in contact with or even close to the animal. Moreover, in cases where vitals are routinely monitored on a moving object within a cage, when it comes to an animal, or a crib, when it comes to an infant human, uses of contact sensors are frustrated by the constant movement. In other instances where a subject may be violent, or is contaminated with a substance or virus, being close to the subject may pose a health threat to the medical practitioner. Accordingly, there remains an unmet need for a system or method for the non-contact vital sign monitoring of a subject that is placed a distance from the subject.

A few non-contact vital sign monitoring solutions have been presented, but all fall short of an acceptable solution for various reasons. Some systems and methods must be placed where they will be integral with some surface in contact with the subject. Some systems and methods are simply are not accurate as surface features such as hair or clothing affect the measuring methods used for vital signs. Other existing technologies suffer from the ability to properly detect a subjects vital sign if a subject is around due to the reflected nature of RF technologies. RF technology by itself further suffers that as the subject distance increases the reflected signal becomes weaker and eventually is indistinguishable from background noise. In addition, existing technologies lack several sensors to properly monitor a subject's vitals and physiological signals.

Thus, there remains an unmet need for a viable solution for at-a-distance non-contact vital sign monitoring that overcomes the aforementioned shortcomings.

SUMMARY OF INVENTION

The present invention provides a viable solution for at-a-distance non-contact vital sign monitoring that overcomes the aforementioned shortcomings.

Aspects of the present invention provide for systems and methods for at-a-distance non-contact vital sign monitoring which properly detect subject's vital signs by correcting the measured signals for reflectance and variations in distance between measurements. In addition, inventive systems, described herein, provide for adequate sensor numbers and types to properly monitor a subject's vitals and physiological signals.

Other aspects include the use of one or more computing devices. Inclusive of such computing devices is at least one processor that is configured to execute a sequence of programmed instructions that cause the processor to implement the one or methods disclosed herein.

Other aspects include the use of one or more data collection systems. Various systems are known in the art. Data may be collected from one or more sensors mounted to one or more platforms or enclosed within one or more housings.

Finally certain aspects of the invention include the use of signal scoring methods. In such embodiments, acquired data and/or information is used for scoring a signal acquired from non-contact vital monitoring assisting in the accurate measurement of various vitals of a subject, including, without limit, a subjects temperature, cardiovascular and respiratory information.

BRIEF DESCRIPTION OF DRAWINGS

Examples illustrative of embodiments of the disclosure are described below with reference to figures attached hereto. In the figures, identical structures, elements or parts that appear in more than one figure are generally labeled with the same numeral in all the figures in which they appear. Dimensions of components and features shown in the figures are generally chosen for convenience and clarity of presentation and are not necessarily shown to scale. Many of the figures presented are in the form of schematic illustrations and, as such, certain elements may be drawn greatly simplified or not-to-scale, for illustrative clarity. The figures are not intended to be production drawings. The figures (FIGS.) are listed below.

Figure 1:
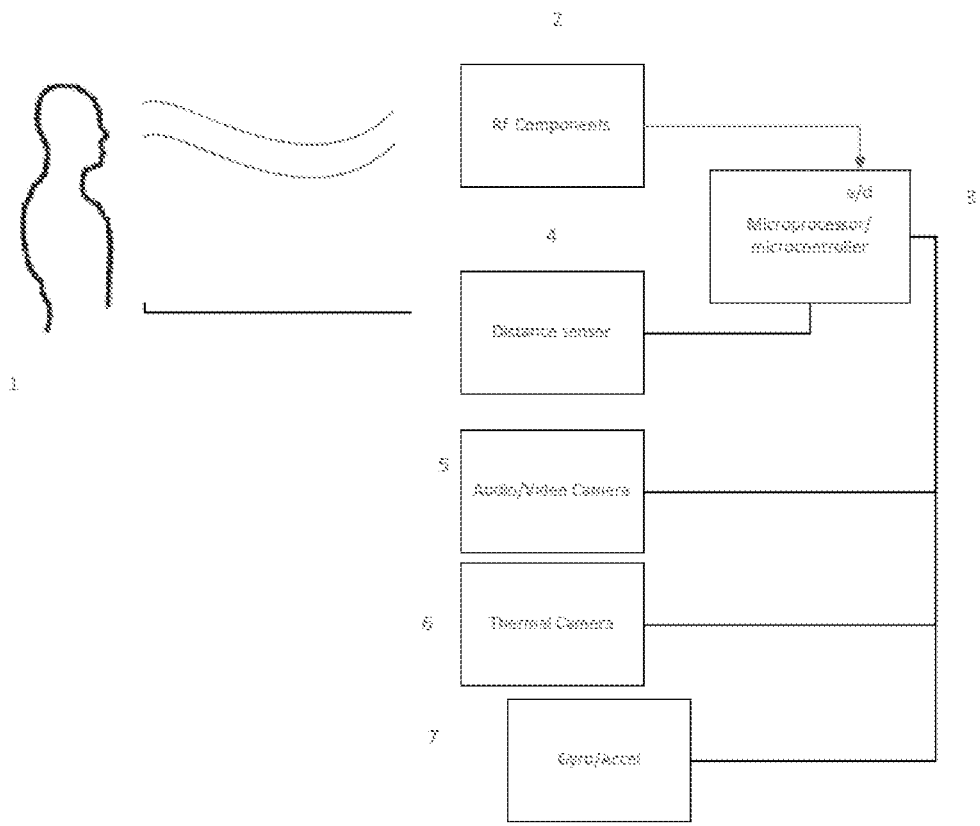
FIG. 1 provides a flow chart illustrating at least one embodiment of the present invention.
Figure 2:
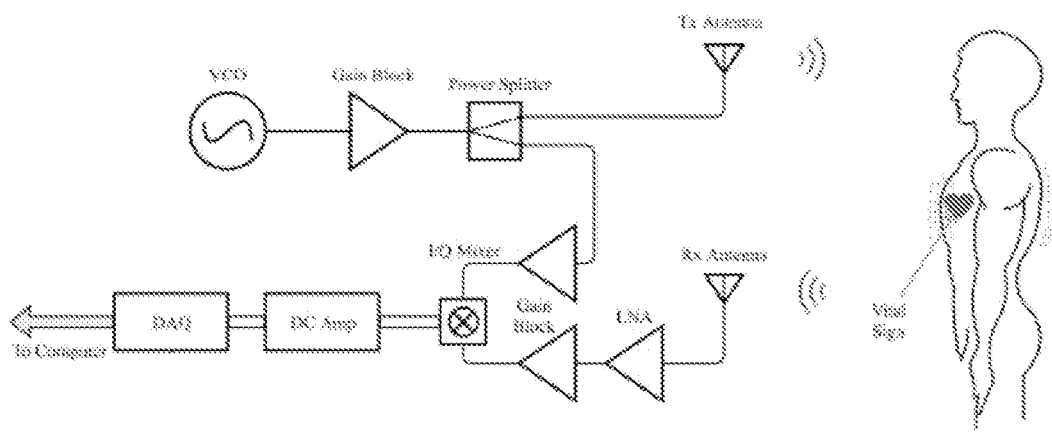
FIG. 2 illustrates a Doppler radar transmitter and receiver system for contact-less vital sign monitoring.
Figure 3:
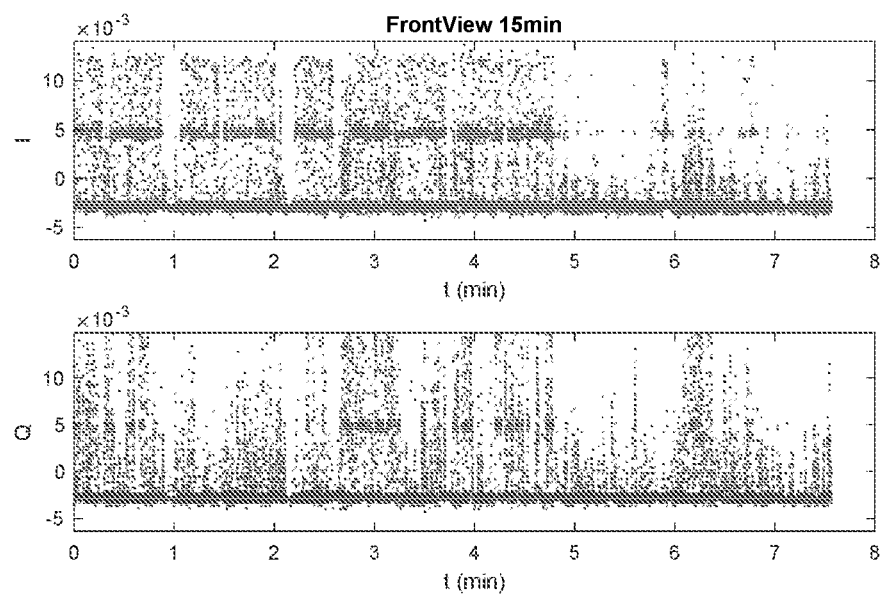
FIG. 3 shows a data plot of I and Q vs Time.
Figure 4:
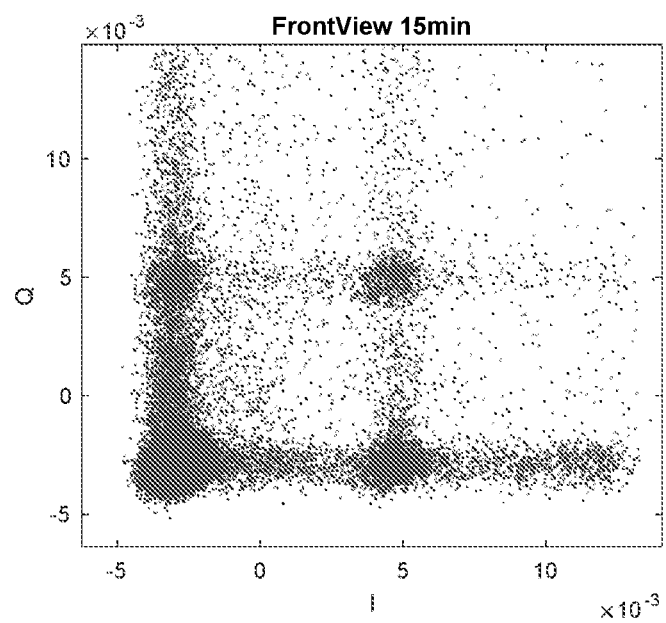
FIG. 4 shows a data plot of I vs Q Scatter Plot.

It should be clear that the description of the embodiments and attached Figures set forth in this specification serves only for a better understanding of the invention, without limiting its scope. It should also be clear that a person skilled in the art, after reading the present specification could make adjustments or amendments to the attached Figures and above-described embodiments that would still be covered by the present invention.

DETAILED DESCRIPTION

The following detailed description is merely exemplary in nature and is in no way intended to limit the scope of the invention, its application, or uses, which may vary. The invention is described with relation to the non-limiting definitions and terminology included herein. These definitions and terminology are not designed to function as a limitation on the scope or practice of the invention, but are presented for illustrative and descriptive purposes only.

The present invention provides for systems and methods for at-a-distance non-contact vital sign monitoring which properly detect subject's vital signs by correcting the measured signals for reflectance and variations in distance between measurements. In addition, inventive systems, described herein, provide for adequate sensor numbers and types to properly monitor a subject's vitals and physiological signals.

The inventive systems and methods further include the use of one or more computing devices. Inclusive of such computing devices is at least one processor that is configured to execute a sequence of programmed instructions that cause the processor to implement the one or methods disclosed herein.

The inventive systems and methods further include the use of one or more data collection systems. Various systems are known in the art. Data may be collected from one or more sensors mounted to one or more platforms or enclosed within one or more housings.

Embodiments of the inventions may further use sensors. For example, distance data may originate from sensors such as Light Detection and Ranging (LiDAR). Other data may be used from RF signal detection and/or reflection and signal adjudication, thermal imaging, infrared, and image capture and analysis, gyroscopes, accelerometers, and other sensors, as may be described in further detail herein.

One or more embodiments of the invention further include the use of signal scoring methods. In such embodiments, acquired data and/or information is used for scoring a signal acquired from non-contact vital monitoring assisting in the accurate measurement of various vitals of a subject, including, without limit, a subjects temperature, cardiovascular and respiratory information.

The present invention further provides improved signal detection of vital monitoring. The signal measurement improvements are a result of using multiple measurement techniques to determine the same vital sign being monitored, and to filter and process the information to correct for movement and reflectance from one measurement interval to the other which may occur naturally by the movement of a subject.

Various terms used throughout the specification and claims are defined as set forth below as it may be helpful to an understanding of the invention.

As used herein, "vital sign" means body temperature, blood pressure, pulse (heart rate), breathing rate (respiratory rate), blood oxygenation of a subject, or other signals which may be used to detect the vital elements determining whether a subject, including data related to heartbeat, breathing, or brain activity.

As used herein, "subject" means any human or animal which has one or more vital signs which may be measured and/or monitored.

System

The present invention is directed to one or more systems intended to be used for at-a-distance non-contact monitoring of vital signs of one or more subject that include one or more sensors and/or vital sign detection methods. Inventive systems include at least one radio frequency (RF) system which included one or more RF transmitter, and at least one RF receiver. Inventive systems further include a computing system which includes at least one computing device. Non-contact vital sign systems use the RF system particularly, the RF transmitter and RF receiver, to acquire one or more reflected RF signals from a subject, then determine using a computer, the Doppler shifts in one or more ranges of acquired data, which when compared to one iteration of signal acquisition to an adjacent iteration of signal acquisition, allows for vital sign acquisition. Analysis of the reflected RF signals can be used to adjudicate certain vital signs of a subject, including heart rate and respiratory rate, as described in patents U.S. Pat. Nos. 7,903,020, 7,848,896, 8,721,554, 8,814,805, 9,200,945, and United States Patent Application 20100204587A1.

In addition to acquisition of RF data, it is appreciated that in some environments, that RF signal acquisition may be compromised by reflectance or movement. Thus, to improve the quality and usability of vital sign acquisition, other data measurements are combined.

In at least one embodiment, an audio/imaging system is incorporated into the system which includes at least one audio/imaging detection device used to acquire information about a subject to resolve vital sign information of that subject. Various audio/imaging detection devices are known in the art and nothing herein is intended to limit the number of or selection of audio and image detection devices made part of an audio/imaging system. In some embodiments of the present invention, the audio/image detection device used in an audio/image system is a video camera with a microphone used to acquire audio and video information of a subject being monitored. In other embodiments an image capture system may be utilize different wavelengths of light that are not visible light.

The audio and imaging information is analyzed using one or more computing methods to resolve respiration, heart rate, or other measured vital signs, and is compared to the vital sign information adjudicated through RF reflectance. It should be appreciated that one or more algorithms may be implemented as part of the audio/imaging system which can resolve one or more desired vital signs using the audio/imaging system or to compare and improve the data reliability of a combination of data acquisition systems described in the present invention and/or incorporated in embodiments of the inventive system. It should be appreciated, that in addition to the methods disclosed herein, traditional signal and image processing techniques, as well as machine learning techniques (e.g., deep learning) can be incorporated into computing methods in order to resolve one or more desired vital signs.

In at least one embodiment, the audio/imaging system is used to detect if the subject is in view of the inventive system. In such embodiments, if a subject is not viewable in frame then audio can be used to detect if a subject is detectable.

In at least one embodiment of the present invention, systems include one or more thermal detection system. The thermal detection system is intended to determine thermal properties of a subject, including non-contact monitoring of a subject's body temperature. It is appreciated that infrared and other filters may be used with audio and imaging system and data acquisition thereof, in order to further assist in vital sign adjudication using and audio/imaging system, which may include, for example, the temperature of the subject. Accordingly, nothing herein is intended to require a separate device for thermal detection if the information may be ascertained using one or more existing systems incorporated into an embodiment of a particular system.

It should be appreciated that one or more algorithms may be implemented as part of the thermal detection system which can resolve one or more desired vital signs using the audio/imaging system or to compare and improve the data reliability of a combination of data acquisition systems described in the present invention and/or incorporated in embodiments of the inventive system.

In at least one embodiment, the thermal detection system is used to detect the presence of the subject if the temperature is greater than or less than ambient so they don't blend in with the surroundings.

Embodiments of the invention may include a signal refinement system of which at least one embodiment includes one or more additional sensors, depending on the desired vital signs to be measured, and depending on the particular use, movement or desired accuracy. In at least one embodiment, the inventive signal refinement system includes one or more of at least one gyroscope or at least one accelerometer. In embodiments where used, the data acquired from an accelerometer and/or gyroscope is used to calculate the angle of the device. This information, when taken into account to the position of the subject being monitored, allows for signal adjustment to account for the angular shifts which may occur in the one or more methods of patient data acquisition obtained.

Other sensors incorporated into at least one embodiment of the signal refinement system include at least one distance sensor for resolving the straight-line distance between a subject and the inventive system used for non-contact vital monitoring. In embodiments where used, the one or more distance sensor is used to acquire the estimated distance to the subject from the point of measurement, or to determine whether a subject is in a detectable area for the system. Acceptable distance sensors may utilize any distance adjudication sensor or method known in the art including without limit, Light Detection and Ranging (LiDAR), acoustic, infrared (IR), video or RF.

It is appreciated that aforementioned systems may individually and collectively communicate to the computing system. It should further be appreciated that for the economy of data bandwidth for the purposes of real-time display, a plurality of computing devices may be incorporated as part of the computing system, including, as a non-limiting example, a computing device dedicated to each method of measurement included in each of the various embodiments described herein.

In certain embodiments, the computing system can be configured to operate in parallel or sequentially in regards to reading from the various sensors. In at least one embodiment, collected data or information from the inventive system may be directed to the computing system for additional processing and/or application of one or more algorithms to be applied on the signals.

In certain embodiments of the present invention, the computing system further includes one or more displays for displaying in real-time the measured, resolved, or adjudicated vital signs being detected.

Computational Algorithms

It is appreciated that in order to provide an objective measure of one or more vital signs, one or more signal methods may be used to refine or improve the acquired signal in order or perform vital sign adjudication. In embodiments using software methods for signal improvement or adjudication, the computing system uses a computer readable medium to store an executable sequence of steps, that when executed performs the desired combination of steps. Without intending to limit the present invention, embodiments may include without limitation, a CPU executing a sequential workflow, a GPU executing a parallel computing workflow, an FPGA or ASIC implementation in hardware, or a hybrid approach such as FPGA+CPU hardware-software co-design implementation.

In at least one embodiment, the RF system utilizes one or more methods for improving the information acquired as a result of the reflected RF signal. One or more methods employed include the evaluation and scoring of the data received. In such embodiments, the score is determined by first evaluating the RF signal based on analog signals received from the transmission and reflected back from a subject by processing the RF signal received through an analog to digital converter (ADC) to provide the heart rate of the subject, then evaluating the signal strength on a scale of 1-10 using a time-scale to determine heart rate, wherein the more inconsistent or fluctuating of a heart rate, the lower the score, and wherein the more consistent or non-fluctuation of heart rate, the higher the score, and finally evaluating the RF signal based on analog signals received from the transmission and reflected back from the subject by processing the RF signal received through an ADC to provide the respiratory rate of the subject, evaluating the signal strength on a scale of 1-10 using a time-scale to determine respiratory rate, wherein the more inconsistent or fluctuating of a respiratory rate, the lower the score, and wherein the more consistent or non-fluctuation of respiratory rate, the higher the score.

In at least one embodiment one or more quality score and signal strength algorithm is used. It should be appreciated that signal strength represents modulation of amplitude of received signal while quality score represents the likelihood of biomedical signal in raw data. Where used signal strength was sufficient using the methods herein to determine where a subject was absent from a field of view but not sufficient to indicate where a patent was present. It was found through implementation that quality score allows for the determination of a present patient in addition to enabling to determine the detection of trustworthy vital signs. As a result, the combination of a quality score and signal strength algorithm provided a surprising result because without the combination the quality score would not be able to detect a patient present.

In at least one embodiment the quality score and signal strength algorithm first provides for clustering and partitioning of "in-phase" and "quadrature" (Q) values from a RF signal received, determining the center of I vs Q polar plot, converting I and Q to phase angle on I vs Q polar plot relative to center determined from clustering and partitioning, assign expected noise (uncertainty) to phase angle at each sample time, applying at least one optimal estimator, for example, without limit, a Kalman filter, to obtain unwound optimal estimate of phase angle vs time from raw phase angle data, utilizing one or more bandpass filter unwound phase angle to extract motion that may be due to metabolic activity, enveloping around the Kalman filtered and bandpass filtered phase angle data is used to calculate signal strength, filtering using low-pass filter (4 Hz cutoff) and down sample (20-fold) phase angle time history, as a data reduction step, converting filtered down-sampled phase angle time history to frequency spectrum vs time by FFT, computing the mean signal strength for each FFT time window for which frequency spectrum was calculated, expressing power for frequency spectrum as sigma's of statistical significance for use in quality analysis, thresholding and grouping statistically significant spectral content (at least 2.5 sigma's significance) to sharpen FFT, scale sharpened FFT by signal strength with inflection point at transition between patient present vs absent data, subtracting the median background and thresholding at zero to factor out noise from FFT, applying a low-pass filter FFT in time and frequency dimensions, converting FFT highest intensity at a given time to calculate quality score using arctangent mapping.

In at least one embodiment for converting time domain signal to frequency domain is FFT, however it should be appreciated that the conversion process includes, without limit, other methods such as the Continuous Wavelet Transform, or a bank of digital filters.

In at least one embodiment deep learning and neural networks are includes as techniques for signal and spectral analysis. It should be appreciated, that where implemented, a deep learning network is trained to report, among other things, signal strength or quality score after being trained on the output from the one or more algorithms described herein.

In at least one embodiment, one or more algorithms are implemented to use with the thermal detection system. Where used, inventive computational methods to be used with the thermal detection system include calculating a subjects temperature based on thermal signatures received from a living body using one or more thermal detection devices, then processing from the temperature information received from the thermal detection device to provide the core temperature of the subject by calculating the strength of the heat signature by scoring the heat strength on a scale of 0 to 10, where inconsistent fluctuation of thermal value based on a time scale is 0 to consistent steady heat signature of 10 on the same time scale.

In at least one embodiment thermal detection devices are calibrated so that the observed temperature of the tear duct corresponds to a given internal temperature.

In certain embodiments, one or more algorithms are implemented to use with the signal refinement system. In at least one embodiment such algorithms are implemented to calculate angle in relation to the device and a subject using one or more of a gyroscope or accelerometers. Signal processing methods include first calculating the gyroscope or accelerometer angle from the difference of the normal plane of the initial direction of the device placed in front of the subject, then processing the angle information received by the gyroscope or accelerometer by assigning a predictable score to the angle information from 0 to 10 where constant movement of the subject based on a time scale is 0 to motionless non-movement of the subject of 10 on the same time scale.

Embodiments having a signal refinement system which utilizes one or more distance sensors, may use the distance measured to manipulate and improve the acquired data from one of the other systems, including, without limit, the RF System Thermal detection system, or audio/visual system. In such embodiments, after the distance data is obtained from the one or more distance sensor, the data is assessed to create a predictable score from 0 to 10 to the distance data where constant movement of the device to the subject value based on a time scale is 0 to stationary position of the device to the subject a value of 10 on the same time scale.

In certain embodiments, one or more computational method are implemented to the data captures by the audio/imaging system. In such embodiments, after audio and/or imaging data is detected, first using Doppler shift determination and other techniques, one or more physiological signs of the subject from the captured audio and imaging data is determined. The data is then improved by processing the audio and imaging data captured by the audio/image detection device to provide the visual and auditory information of the subject to the device. Then by assigning a predictable score from 0 to 10 of the audio data where constant environmental sounds impacting the vital signs of the subject based on a time scale is 0 to negligible audible information of the subject a value of 10 on the same time scale, in addition to assigning a score from 0 to 10 of the imaging data where constant movement impacting the vital signs of the subject based on a time scale is 0 to negligible movement information of the subject a value of 10 on the same time scale.

It is appreciated that of the one or more methods employed for improving signal reliability or interpretation of data by the computing system may be combined in any number based on the devices and systems employed in a particular embodiment. Where combined the independent scores of each of the various systems is combined to into to yield a combine score from 0 to 10 with each number accompanied by a one decimal point. i.e., 0.0.1, 0.2 . . . 9.8, 9.9, 10, which is employed to predict vital sign data.

In at least one or more embodiments, after the one or more scores is received from the one or more data sources, the weighted averages of all combined scores are calculated to display one value on a presentation screen.

In at least one or more embodiments if the combined values of all scores ranges from 0 to 9.9 with 0 being the system is not transmitting any independent input to 9.9 where 9.9 indicates that the Heart Rate, Respiration Rate and Temperature reading displayed on the screen is very accurate and should be considered as the values to provide treatment decisions based on diagnostic condition of subject.

In at least one embodiment, predicting a score associated with the remote sensing of an subjects vital signs (Heart Rate, Respiration and Temperature) simultaneously to determine the strength of the multiple signals based on environmental factors that they may impact the measurements of the non-contact monitoring of vitals.

It should be appreciated that where scoring is used in any of the methods described herein, the score of 10 is a theoretical value that cannot be attained. In addition, it should be further appreciated that the score of 0 is a state where no power is provided to perform any of the sensing capability of the device.

It should further be appreciated that when one or more scoring methods are employed in certain embodiments, the scoring is based on a time scale that starts and ends at the same timestamp.

In some embodiments, the combination of independent scoring is dropped into the first pass or second pass buckets, a lowest combined scoring of first pass makes the second pass scoring irrelevant, the relevancy of second pass scoring climbs with the first pass score increments, and second pass scoring decelerates quicker than the first pass score decrements.

It should be appreciated that in some embodiments that it may be necessary to apply a higher weighing factor to data acquired through the signal enhancement system and/or the audio/imaging system and indicated as first pass. It should be appreciated that in some embodiment that the lower weightage is provided to vital sign adjudication, such as heart rate, respiration rate and temperature, and indicated as second pass based on calculation of first pass scoring.

OTHER EMBODIMENTS

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient road map for implementing the exemplary embodiment or exemplary embodiments. It should be understood that various changes can be made in the function and arrangement of elements without departing from the scope as set forth in the appended claims and the legal equivalents thereof.

The invention claimed is:

1. A system for at-a-distance non-contact monitoring of one or more vital signs of a subject, the system comprising:
at least one detection device that detects one or more signals from a living body without any physical contact to said living body, wherein said detection device comprises at least one RF transmitter and at least one RF receiver, and wherein said one or more signals is an RF signal transmitted from said RF transmitter and received by said RF receiver from the reflection of the transmitted RF signal from said living body;
at least one computing device for receiving said one or more signals from said at least one detection device, and analyzing said one or more signals to estimate one or more vital signs of a said living body, wherein said one or more vital signs comprise heart rate and respiratory rate; and
at least one monitoring device allowing one or more user to monitor said one or more vital signs computed by said at least one computing device;
wherein the at least one computing device contains a non-transitory computer readable medium containing instructions, that when executed perform the method of:
transmitting the RF signal from the at least one RF transmitter;
receiving the RF signal reflected from said living body by the at least one RF receiver;
analyzing the RF signal received by the one or more RF receiver to detect one or more vital sign of said living body;
determining a signal strength and quality score of the one or more vital sign identified in the RF signal, wherein determining the signal strength and quality score further comprises:
a) evaluating the one or more RF signal based on analog signals received from the RF signal transmitted from said RF transmitter and reflected back from said living body by processing the RF signal received through a digital to analog converter (DAC) to provide the heart rate of said living body, evaluating the signal strength and generating a scale of signal strength using a time-scale to determine the heart rate, wherein the more inconsistent or fluctuating of the heart rate, the lower the quality score, and wherein the more consistent or non-fluctuation of the heart rate, the higher the quality score; and
b) evaluating the one or more RF signal based on analog signals received from the RF signal transmitted from said RF transmitter and reflected back from said living body by processing the one or more RF signal received through the DAC to provide the respiratory rate of said living body, evaluating the signal strength and generating a scale of signal strength using a time-scale to determine the respiratory rate, wherein the more inconsistent or fluctuating of the respiratory rate, the lower the quality score, and wherein the more consistent or non-fluctuation of the respiratory rate, the higher the quality score; and
communicating a filtered one or more vital signs of said living body being monitored to said at least one monitoring device.

2. The system of claim 1 further comprising at least one distance sensor for detecting the distance between said living body and said at least one detection device.

3. The system of claim 1 further comprising an audio detection device and an image detection device.

4. The system of claim 1 further comprising a thermal detection device for measuring temperature of said living body.

5. The system of claim 1 further comprising at least one RF signal modulator and at least one RF signal demodulator.

6. The system of claim 1 further comprising a housing for enclosing one or more of at least one detection device, at least one computing device, or combinations thereof.

7. The system of claim 1 wherein said at least one monitoring device is one or more of an audio interface, an image display, a data transmitter, a mobile device, a data storage system, or combinations thereof.

8. The system of claim 2 wherein said at least one distance sensor is Light Detection and Ranging (LiDAR).

9. A system for at-a-distance non-contact monitoring of one or more vital signs of a subject, the system comprising:
at least one detection device that detects one or more signals from a living body without any physical contact to said living body, wherein said detection device comprises at least one RF transmitter and at least one RF receiver, and wherein said one or more signals is an RF signal transmitted from said RF transmitter and received by said RF receiver from the reflection of the transmitted RF signal from said living body;
at least one computing device for receiving said one or more signals from said at least one detection device, and analyzing said one or more signals to estimate one or more vital signs of said living body, wherein said one or more vital signs comprise heart rate and respiratory rate;
at least one monitoring device allowing one or more user to monitor said one or more vital signs computed by said at least one computing device;
at least one distance sensor to detect the distance between said at least one living body and said at least one detection device; and
at least one RF signal demodulator;
wherein the at least one computing device contains a non-transitory computer readable medium containing instructions, that when executed perform the method of:
transmitting the RF signal from the at least one RF transmitter;
receiving the RF signal reflected from said living body by the at least one RF receiver;
analyzing the RF signal received by the one or more RF receiver through the use of the RF signal demodulator to detect one or more vital sign of said living body;
calculating the distance between said detection device and said living body;
determining a signal strength and quality score of the one or more vital sign identified in the RF signal, wherein determining the signal strength and quality score further comprises:
a) evaluating the one or more RF signal based on analog signals received from the RF signal transmitted from said RF transmitter and reflected back from said living body by processing the RF signal received through a digital to analog converter (DAC) to provide the heart rate of said living body, evaluating the signal strength and generating a scale of signal strength using a time-scale to determine the heart rate, wherein the more inconsistent or fluctuating of the heart rate, the lower the quality score, and wherein the more consistent or non-fluctuation of the heart rate, the higher the quality score; and b) evaluating the one or more RF signal based on analog signals received from the RF signal transmitted from said RF transmitter and reflected back from said living body by processing the one or more RF signal received through the DAC to provide the respiratory rate of said living body, evaluating the signal strength and generating a scale of signal strength using a time-scale to determine the respiratory rate, wherein the more inconsistent or fluctuating of the respiratory rate, the lower the quality score, and wherein the more consistent or non-fluctuation of the respiratory rate, the higher the quality score;

extrapolating and filtering the physiological signals of said living body being monitored using the information calculated using the distance sensor;

communicating the filtered one or more vital signs of said living body being monitored to said at least one monitoring device.

10. The system of claim 9 further comprising an audio detection device and an image detection device.

11. The system of claim 9 further comprising a thermal detection device for measuring temperature of said living body.

12. The system of claim 9 further comprising at least one RF signal modulator.

13. The system of claim 9 further comprising a housing for enclosing one or more of said at least one detection device, at least one computing device, at least one RF demodulator, at least one distance sensor, or combinations thereof.

14. The system of claim 9 wherein said at least one monitoring device is one or more of an audio interface, an image display, a data transmitter, a mobile device, a data storage system, or combinations thereof.

15. The system of claim 9 wherein said at least one distance sensor is Light Detection and Ranging (LiDAR).

16. A system for at-a-distance non-contact monitoring of one or more vital signs of a subject, the system comprising:

at least one detection device that detects one or more signals from a living body without any physical contact to said living body;

at least one computing device for receiving said one or more signals from said at least one detection device, and analyzing said one or more signals to estimate one or more vital signs of said living body, wherein said one or more vital signs comprise heart rate, respiratory rate, or body temperature; and at least one monitoring device allowing one or more user to monitor said one or more vital signs computed by said at least one computing device;

wherein the at least one computing device contains a non-transitory computer readable medium containing instructions, that when executed perform the method of:

receiving one or more data signal from the one or more detection device monitoring said living body;

analyzing the one or more data signal received by said one or more detection device to detect one or more vital sign of said living body being monitored;

determining a signal strength and quality score of the one or more vital sign identified in the one or more data signal, wherein determining the signal strength and quality the score further comprises:

a) evaluating the one or more data signal received from the one or more detection device monitoring said living body to determine the heart rate of said living body, evaluating the signal strength of the heart rate and generating a scale of the signal strength using a time-scale to determine the heart rate, wherein the more inconsistent or fluctuating of the heart rate, the lower the quality score, and wherein the more consistent or non-fluctuation of the heart rate, the higher the quality score; and b) evaluating the one or more data signal received from the one or more detection device monitoring said living body to determine the respiratory rate of said living body, evaluating the signal strength of the respiratory rate and generating a scale of the signal strength using a time-scale to determine the respiratory rate, wherein the more inconsistent or fluctuating of the respiratory rate, the lower the quality score, and wherein the more consistent or non-fluctuation of the respiratory rate, the higher the quality score;

communicating the one or more vital signs of said living body being monitored to said at least one monitoring device.

17. The system of claim 16 wherein said detection device is one or more of at least one RF transmitter, at least one RF receiver, at least one audio detection device, at least one image detection device, at least one thermal detection device, or combinations thereof.

18. The system of claim 16 further comprising at least one distance sensor for measuring the distance between said living body and said at least one detection device.

19. The system of claim 16 further comprising a housing for enclosing at least one of said at least one detection device, or said at least one computing device.

20. The system of claim 16 wherein said at least one monitoring device is an audio interface, an image display, a data transmitter, a mobile device, or a data storage system.

* * * * *